US012779157B2

(12) United States Patent
Eskozido et al.

(10) Patent No.: US 12,779,157 B2
(45) Date of Patent: Nov. 3, 2026

(54) RESPIRATORY SUPPORT DEVICE AND CARTRIDGE FOR USE THEREWITH

(71) Applicant: RESPISAFE LTD., D.N Hof Ashkelon (IL)

(72) Inventors: Almog Eskozido, Kfar Maimon (IL); Maor Glasnip, Petah Tikva (IL)

(73) Assignee: RESPISAFE LTD., D.N Hof Ashkelon (IL)

( * ) Notice: Subject to any disclaimer, the term of this patent is extended or adjusted under 35 U.S.C. 154(b) by 512 days.

(21) Appl. No.: 18/562,516

(22) PCT Filed: May 19, 2022

(86) PCT No.: PCT/IL2022/050525
§ 371 (c)(1),
(2) Date: Nov. 20, 2023

(87) PCT Pub. No.: WO2022/244009
PCT Pub. Date: Nov. 24, 2022

(65) Prior Publication Data

US 2024/0181187 A1 Jun. 6, 2024

Related U.S. Application Data

(60) Provisional application No. 63/190,884, filed on May 20, 2021.

(51) Int. Cl.
*A61M 16/00* (2006.01)

(52) U.S. Cl.
CPC .... *A61M 16/0084* (2014.02); *A61M 16/0078* (2013.01); *A61M 2202/0208* (2013.01)

(58) Field of Classification Search
CPC .......... A61M 16/0084; A61M 16/0078; A61M 2202/0208; A61M 16/0075; A61M 2205/583; A61M 2205/586; A61M 16/06; A61M 2205/3379; A61M 16/209; A61M 2016/0027; A61M 2202/0225; A61M 16/00; A61M 16/0081; A61M 16/0611; A61M 16/08
See application file for complete search history.

(56) References Cited

U.S. PATENT DOCUMENTS

| | | | | |
|---|---|---|---|---|
| 4,349,015 A * | 9/1982 | Alferness | A61H 9/0078 128/205.16 |
| 4,870,962 A | 10/1989 | Sitnik | |
| 5,787,880 A | 8/1998 | Swanson et al. | |
| 8,534,282 B2 * | 9/2013 | Bergman | A61M 16/0078 128/205.16 |

(Continued)

FOREIGN PATENT DOCUMENTS

| | | |
|---|---|---|
| CN | 103751894 A | 4/2014 |
| CN | 203802914 U | 9/2014 |

(Continued)

*Primary Examiner* — Elliot S Ruddie
(74) *Attorney, Agent, or Firm* — Whitestone Law, PLLC

(57) ABSTRACT

Some embodiments relate to a respiratory support device for use with an inflatable and deflatable cartridge. The device can include a cartridge receiving portion for removably attaching to the inflatable and deflatable cartridge; and an actuating mechanism configured for selectively inflating and deflating the inflatable and deflatable cartridge, when received in the cartridge receiving portion.

14 Claims, 13 Drawing Sheets

(56) References Cited

U.S. PATENT DOCUMENTS

| | | | |
|---|---|---|---|
| 9,861,775 B1 | 1/2018 | Farmer et al. | |
| 2006/0266358 A1 | 11/2006 | Hoogland | |
| 2014/0318544 A1 | 10/2014 | Murphy et al. | |
| 2020/0345967 A1 | 11/2020 | Merrell et al. | |
| 2021/0299372 A1* | 9/2021 | Maguire | A61M 16/06 |

FOREIGN PATENT DOCUMENTS

| | | |
|---|---|---|
| CN | 108310565 A | 7/2018 |
| CN | 110917456 A | 3/2020 |
| CN | 211434595 U | 9/2020 |
| CN | 112402754 A | 2/2021 |

* cited by examiner

RESPIRATORY SUPPORT DEVICE AND CARTRIDGE FOR USE THEREWITH

CROSS REFERENCE TO RELATED APPLICATIONS

This application is a national phase filing under 35 C.F.R. § 371 of and claims priority to PCT Patent Application No PCT/IL2022/050525, filed on May 19, 2022, which claims priority benefit under 35. U.S.C. § 119 of U.S. Patent Application No. 63/190,884, filed on May 20, 2021, the contents of each of which are hereby incorporated in their entireties by reference.

TECHNOLOGICAL FIELD

The presently disclosed subject matter relates to respiratory support devices for providing respiratory support to a patient; particularly, the presently disclosed subject matter relates to respiratory support devices configured for use with removable cartridges and such removable cartridges for providing respiratory support to a patient with improved sterility.

BACKGROUND

Resuscitation devices are well known and commonly used to provide breathing (respiration) support to a patient. Such support using resuscitation devices generally involve inflating and deflating a bag that is connected to a mask via an air tube, which mask provides the air/oxygen pushed from the bag (for instance, while deflation thereof) to the patient.

Accordingly, as such respiratory support devices are to be used in medical environments, these devices should ensure that sterile air be provided to the patient. Also, as such devices are to be used in emergency situations, these devices should be easy and convenient to use.

US patent application No. US2020345967 discloses a respiratory device for providing respiratory support to a patient. The device includes an expandable bag portion and a connection member in fluid communication with the expandable bag portion. The expandable bag portion includes an air intake valve and has an adjustable predetermined tidal volume. The connection member includes a positive end expiratory pressure (PEEP) valve, a PEEP controller configured to control the pressure of the PEEP valve, a two-way valve configured to allow air to move from the expandable bag portion in a first direction and through the PEEP valve in an opposing direction, a pressure relief valve configured to vent excess pressure from the connection member to an external environment, and a patient breathing interface.

US patent application No. US2006266358 discloses a hand operated resuscitator that has a bellows for the hand pumping of air or oxygen. The resuscitator is provided with a limiting mechanism that prevents the full expansion of the bellows so that the amount of air or oxygen delivered to the patient can be limited.

U.S. Pat. No. 9,861,775 discloses an emergency resuscitation apparatus with external air volume control that includes a housing having top and bottom plates pivotally coupled so as to siphon air into an internal reservoir via an inflow port and propel air out through an outlet port to a patient. A volume control plate is coupled to the bottom plate externally adjacent a second end wall, the volume control plate having a plurality of volume selectors. An air volume limit arm is operatively coupled to the volume control plate and selectively movable between and coupled to a selected volume selector. A volume limiting flange associated with the volume limit arm are positioned in a common vertical plane with top plate such that the volume limit flange prevents upward movement of the top plate beyond the setting of the volume limit arm so as to regulate a quantity of air being expelled.

US patent application No. US2014318544 discloses a manually actuated, self-inflating bag valve mask that provides a tidal volume to the patient and controls the rate of ventilation of the patient.

U.S. Pat. No. 4,870,962 discloses a manually actuated, self-distending, self-inflating resuscitator bag that is substantially shaped like a pleated, handle less bellows where the pleats act like a spring following compression to rapidly re-inflate the bag to its fully recovered state, and that the flat sides of the bellows enable the operator to easily pump the bag with one hand or a knee as there is no tendency to roll away during the compression cycle.

CN 110917456 discloses a medical breathing machine capable of being used normally under no driving power condition. The breathing machine includes a supporting shell, a supporting plate is fixedly installed on the right side of the supporting shell, a ventilation tube and an expiration tube are fixedly connected to the top of the supporting plate, a slideway is fixedly connected to the interior of the ventilation tube, and the top of the slideway is fixedly installed at the bottom of an arc-shaped block; and the outer side of the arc-shaped block passes through the side wall of the ventilation tube, a protruding block is fixedly and movably installed on the outer side of the arc-shaped block, and a cover plate is fixedly installed at the top of the arc-shaped block. An inlet of a movable block loses resistance, air is sucked inwards, magnetic blocks are squeezed out to suck out the protruding block, the bottom of the movable block is compressed towards the protruding block under the action of magnetic force, the air is compressed to the interior of the arc-shaped block for breath, after the interior of the movable block loses air, the magnetic blocks are retracted into a fold, the protruding block is repelled by the magnetic blocks and is retracted into the arc-shaped block, so that the cyclic breathing operation is completed; and the breathing machine can continue assisting breath of a patient within a period of time after losing electrical power.

There is a need of advanced respiratory support devices with improved sterility and ease of use.

GENERAL DESCRIPTION

The presently disclosed subject matter relates to respiratory support devices for use with removable cartridges to ensure the sterility of the air being delivered to the patients. For instance, the removable cartridges can be replaced with a new and sterilized cartridge before every use of the respiratory support device. The presently disclosed subject matter also relates to removable cartridges to be used with such respiratory support device. The removable cartridges can be inflated and deflated when positioned in the respiratory support device and can be removed and disposed after every use to be replaced by a new and sterilized one. The presently disclosed subject matter further relates to respiratory support devices for use with a removable cartridge (similar to the above-mentioned ones) or a fixed inflatable and deflatable bag having a structure that is easier and more convenient to use with minimal forces for efficient delivery of air to the patient via the respiratory support devices.

According to a first aspect of the presently disclosed subject matter, there is provided a respiratory support device for use with an inflatable and deflatable cartridge, said device comprising: a cartridge receiving portion for removably attaching to the inflatable and deflatable cartridge; and an actuating mechanism configured for selectively inflating and deflating the inflatable and deflatable cartridge, when received in the cartridge receiving portion.

Optionally, the cartridge receiving portion can define a volume configured to contain at least an inflatable and deflatable portion of the inflatable and deflatable cartridge, said volume being expandable and contractable by means of said actuating mechanism.

Optionally, the respiratory support device can further comprise a first arm and a second arm defining at least partially said cartridge receiving portion therebetween.

In some examples, the first and second arms may be free of any direct connections with each other, and can be independently operated by a user to change a distance therebetween, thereby expanding or contracting the volume defined by the cartridge receiving portion. In this case, almost whole of the length of the arms can constitute the cartridge receiving portion, and portions thereof configured to be held by the user for the above-mentioned operation thereby constituting the actuating mechanism.

Optionally, the first and the second arms can be operatively connected to each other and can be configured to pivot with respect to each other. The actuating mechanism can be operable to pivot the first and the second arms with respect to each other for said inflating and deflating the inflatable and deflatable cartridge, when the inflatable and deflatable cartridge is received in the cartridge receiving portion.

Optionally, the first arm can have a first proximal portion and a first distal portion spaced from said first proximal portion along a device longitudinal axis of the device, and the second arm can have a second proximal portion and a second distal portion spaced from said second proximal portion along the device longitudinal axis, wherein the first and the second distal portions define therebetween the cartridge receiving portion, and the first and the second proximal portions can constitute at least a part of the actuating mechanism.

Optionally, the first arm can comprise a first central portion between the first proximal portion and the first distal portion and the second arm can comprise a second central portion between the second proximal portion and the second distal portion, the two arms being pivotally connected to each other at their central portions, defining a pivot axis perpendicular to a device longitudinal axis of the device.

According to a second aspect of the presently disclosed subject matter, there is provided an inflatable and deflatable cartridge for use with a respiratory support device, said cartridge being configured to be removably received in the respiratory support device, and to be selectively inflated and deflated by an actuating mechanism of the respiratory support device, when received in the respiratory support device, to inhale air, when inflated, and exhale the air, when deflated.

According to a third aspect of the presently disclosed subject matter, there is provided a kit comprising: a respiratory support device according to the first aspect or any of the examples thereof described herein; and one or more disposable inflatable and deflatable bag cartridge according to the second aspect or any of the examples thereof described herein. Optionally, the kit can further comprise a mask and an air tube configured to establish a fluid connection between the cartridge and the mask.

According to a fourth aspect of the presently disclosed subject matter, there is provided a respiratory support device for operating an inflatable and deflatable bag to inhale and exhale air, said device comprising: an actuating mechanism configured for selectively inflating and deflating said inflatable and deflatable bag; a first arm having a first proximal portion constituting at least a part of the actuating mechanism, a first distal portion spaced from said first proximal portion along a device longitudinal axis of the device, and a first central portion between the first proximal and distal portions; and a second arm having a second proximal portion constituting at least a part of the actuating mechanism, a second distal portion spaced from said second proximal portion along the device longitudinal axis and defining together with the first distal portion a volume configured to be expandable and contractable by means of said actuating mechanism, and a second central portion between the second proximal and distal portions; wherein said first and second arms cross each other and are pivotally connected to each other at said respective central portions, said actuating mechanism being operable to pivot the first and second arms with respect to each other.

The respiratory support device according to the fourth aspect can be configured to be used with the removable inflatable and deflatable cartridges, such as those according to second aspect, in a similar manner as the respiratory support device according the first aspect, wherein the inflatable and deflatable bag can constitute an inflatable and deflatable portion of the removable cartridge. In such examples, the device can comprise a cartridge receiving portion defined by said volume between the first and second distal portions, said cartridge receiving portion being configured for removably attaching to the removable cartridge.

The respiratory support device according to any of the first and the fourth aspects can include one or more of the below mentioned features:

Optionally, the first arm and the second arm cross each other to form an X-like structure, or more particularly to a plier-like structure.

Optionally, the actuating mechanism can be operable to expand said volume thereby inflating the inflatable and deflatable cartridge (or bag thereof) and to contract said volume thereby deflating the inflatable and deflatable cartridge (or bag thereof).

Optionally, the cartridge receiving portion can be defined between at least a majority of length of the first and the second distal portions.

Optionally, the first distal portion (or the portion of the first arm constituting a part of the cartridge receiving portion) can comprise a first receptacle facing the second arm, and the second distal portion (or the portion of the first arm constituting a part of the cartridge receiving portion) can comprise a second receptacle facing the first arm, wherein said first and the second receptacles define at least partially the cartridge receiving portion.

Optionally, each of the first and the second receptacles can be configured to removably engage a corresponding one of a first and a second catcher of the inflatable and deflatable cartridge, thereby attaching the cartridge receiving portion to the inflatable and deflatable cartridge.

Optionally, the first and the second receptacles can be elongated receptacles extending along length of the corresponding distal portions (or the cartridge receiving portion), formed either as a single elongated receptacle or constituted by two or more discrete receptacles positioned along said length.

Optionally, the first and second receptacles can extend along at least a majority of the cartridge receiving portion in a direction along a device longitudinal axis of the device.

Optionally, the first and second receptacles can extend along whole of length of the cartridge receiving portion in a direction along a device longitudinal axis of the device.

Optionally, each of said first and second receptacles can have a length corresponding to respective catcher of the inflatable and deflatable cartridge.

Optionally, the first and second receptacles can be at least partially aligned with respect to each other in a plane extending along a device longitudinal axis of the device.

Optionally, the actuating mechanism can be operable to displace the device between an open state corresponding to an inflated state of the inflatable and deflatable cartridge (or bag thereof) when positioned in the cartridge receiving portion and a closed state corresponding to a deflated state of the inflatable and deflatable cartridge (or bag thereof) when positioned in the cartridge receiving portion.

Optionally, at the closed state, said volume is contracted and at the open state, said volume is expanded.

Optionally, the actuating mechanism can be operable to expand said volume thereby inflating the cartridge (or bag thereof) and to contract said volume thereby deflating the cartridge (or bag thereof), when the cartridge is positioned in the cartridge receiving portion.

Optionally, the cartridge receiving portion can be configured to receive the inflatable and deflatable cartridge at least in the closed state of the device.

Optionally, at the closed state, the first and the second receptacles can extend parallel to each other.

Optionally, the first and the second receptacles can be configured to slidingly engage a corresponding one of a first and a second catcher of the inflatable and deflatable cartridge in a direction along a device longitudinal axis of the device.

Optionally, the device can further comprises a limiter configured for limiting an extent of at least one of expansion and contraction of said volume by the actuating mechanism.

Optionally, the device can further comprise a selection mechanism configured to facilitate selection of said extent from a plurality of options.

Optionally, the device can further comprise a stopper configured to maintain said volume to a minimum non-zero volume when contracted.

Optionally, the device can further comprise a biasing element configured to bias the device into the open state.

Optionally, the actuating mechanism can be operable against said bias by a single hand of a user.

Optionally, the actuating mechanism can comprises an electrically/electronically operated actuator configured to expand and contract said volume.

Optionally, the device can comprise a device locking element configured to engage a corresponding cartridge locking element of the inflatable and deflatable cartridge for removably locking, and thereby attaching, the inflatable and deflatable cartridge in the cartridge receiving portion to thereby firmly hold the inflatable and deflatable cartridge in the cartridge receiving portion at least during operation thereof.

Optionally, the device locking element can be positioned at at least one of the first and second arms.

Optionally, the device can be configured to maintain a gap between the cartridge receiving portion and the inflatable and deflatable cartridge when positioned therein, said gap being configured to allow a user to insert a finger therein to remove the inflatable and deflatable cartridge from the cartridge receiving portion.

Optionally, the limiter can be positioned at connection point at said central portions of the two arms.

Optionally, each of the first and the second proximal portions can include a corresponding handle configured to be held by a user for said pivoting the first and second arms, the proximal portions thereby constituting the respective parts of the actuating mechanism.

Optionally, at the open state, a distance between the handles can be such that the handles are configured to be held and operated by one hand by the user.

Optionally, at the closed state, the handles can at least partially abut each other.

Optionally, at the closed state, the first and the second distal portions can extend substantially parallel to each other.

Although all the examples of the respiratory support device according to the fourth aspect have been described as being configured for use with a removable cartridge, it is to be understood that according to some other examples, the respiratory support device according to the fourth aspect can have a fixed inflatable and deflatable bag. In such examples, the receptacles can include, or even be replaced by, fixed connection elements configured to fixedly attach the inflatable and deflatable bag. Further, in such examples, the above description about the inflation and deflation of the cartridge (or bag thereof) would apply to that fixed bag.

The inflatable and deflatable cartridge according to the second aspect can be configured to be used with the respiratory support device according to any of the first and the fourth aspects (those examples of the fourth aspect where the respiratory support device of the fourth aspect is configured for use with a removable cartridge), as described herein below. The cartridge according to the second aspect can include one of more of the following features.

Optionally, the cartridge can comprise a first support base, a second support base spaced from the first support base in a direction perpendicular to a cartridge longitudinal axis of the cartridge, and an inflatable and deflatable bag portion disposed between, and fixedly connected to, the first and the second support bases.

Optionally, the first and the second support bases can extend along at least a majority of length of the inflatable and deflatable bag portion in a direction along the cartridge longitudinal axis.

Optionally, the first and the second support bases can extend along almost whole of length of the inflatable and deflatable bag portion in a direction along the cartridge longitudinal axis.

Optionally, the first support base can comprise a first catcher configured to removably engage within a corresponding first receptacle of the respiratory support device, and the second support base comprises a second catcher configured to be removably received within a corresponding second receptacle of the respiratory support device.

Optionally, the first and the second catchers can be elongated catchers extending along length of the corresponding bases in a direction along the cartridge longitudinal axis, formed either as a single elongated catcher or constituted by two or more discrete catchers positioned along said length.

Optionally, the first and second catchers can extend along at least a majority of length of the respective support base.

Optionally, the first and second catchers can extend along almost whole of length of the respective support base.

Optionally, length of each of the first and second catchers can correspond to length of the corresponding receptacle of the respiratory support device.

Optionally, the inflatable and deflatable bag portion can be configured to be inflated by pulling at least one of the support bases away from the other one of the support bases, and to be deflated by pushing at least one of the support bases towards the other one of the support bases.

Optionally, the cartridge can have an accordion-like structure.

Optionally, at a deflated state of the cartridge, the first and second support bases can extend parallel to each other.

Optionally, the cartridge can be configured to be removably received in the respiratory support device in the deflated state.

Optionally, the cartridge can comprise an inlet opening, an outlet opening, and an air flow path extending between and including the inlet and the outlet openings.

Optionally, the cartridge can be configured to inhale the air through the inlet opening when the cartridge is inflated and to exhale the air through the outlet opening when the cartridge is deflated.

Optionally, at least one of the inlet opening and the outlet opening can face away from the respiratory support device, when the cartridge is received in the respiratory support device.

Optionally, the inflatable and deflatable bag portion can comprise a bag interior volume in fluid communication with the inlet opening and the outlet opening and defining at least a part of the air flow path.

Optionally, at least one of the inlet opening and the outlet opening can be formed in at least one of the first and the second support bases, and the air flow path extends through said at least one of the first and the second support bases.

Optionally, the inflatable and deflatable bag portion can be configured to inhale the air through the inlet opening when the cartridge is inflated and to exhale the air through the outlet opening when the cartridge is deflated.

Optionally, the inlet opening, the outlet opening, and the air flow path can be configured to be fluidly isolated from the respiratory support device when the cartridge is received in the respiratory support device.

Optionally, the outlet opening can be connectable to an air tube configured to deliver the air to a patient.

Optionally, the cartridge can comprise an opening base including said outlet opening, said opening base configured to provide a stabilized connection between the outlet opening and said air tube.

Optionally, the opening base can be integrally formed with one of the first and the second support bases.

Optionally, the opening base can be articulated to one of the first and the second support bases. The one of the support bases can be configured to remain stationary during the inflation and deflation of the cartridge.

Optionally, the inflatable and deflatable bag portion can be configured to be inflated by pulling other one of the support bases away from said one of the support bases, and to be deflated by pushing the other one of the support bases towards said one of the support bases.

Optionally, the cartridge can comprise a cartridge locking element configured to engage a corresponding device locking element of the respiratory support device for removably locking the cartridge in the respiratory support device to thereby firmly hold the cartridge in the respiratory support device at least during operation thereof.

Optionally, the cartridge locking element can be positioned at at least one of the first and second support bases.

The cartridge locking element can be a locking recess and the device locking element can be a spring pin configured to be removably locked in the locking recess. In other examples, the device receiving locking element can be a locking recess and the cartridge locking element can be a spring pin configured to be removably locked in the locking recess.

The features related to lengths, that whole or majority of length of the bag portion is covered by the support bases, the catchers extend along whole or majority of the lengths of the support bases, and that the lengths of the catchers and the receptacles correspond to each other facilitates an efficient inflation and deflation of the bag portion thereby consuming whole of the bag interior volume. This results in more efficient respiratory support with minimal force, as with a definite amount of the force, the whole of the bag interior volume is utilized, as compared to what would have been utilized in case the bag portion were not to be held throughout its length. Furthermore, these features ensure better support and holding strength for the cartridge in the respiratory support device. Therefore, in the context of the present application, the terms whole or, and majority of, are to understood as necessary as well as enough to serve the above-mentioned purposes. For instance, the term almost whole of the length is to be understood herein as the minimum length that would sufficiently serve the above-mentioned purpose and can be 90-100%, 80-90%, 70-80%, 60-70%, or 51-60% of the length that it corresponds to.

It is to be understood herein that the term parallel and/or substantially parallel when used in relation to the portions of the arms and receptacles of the respiratory support device and support bases and catchers of the cartridge intends to mean that these elements are parallel at least enough, if not absolutely parallel, to facilitate sliding insertion of the cartridge into the cartridge receiving portion and sliding engagement of the catchers with the cartridge. In some implementations, these elements may not be exactly parallel but can still allow the sliding insertion of the cartridge/catchers with respect to the cartridge receiving portion/receptacles, an such implementations are to be understood as falling within the spirit and scope of the term parallel. In other words, the term parallel is not limited to absolutely zero angle between these elements, and this be considered that a practical tolerance falls within the scope of the term parallel.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
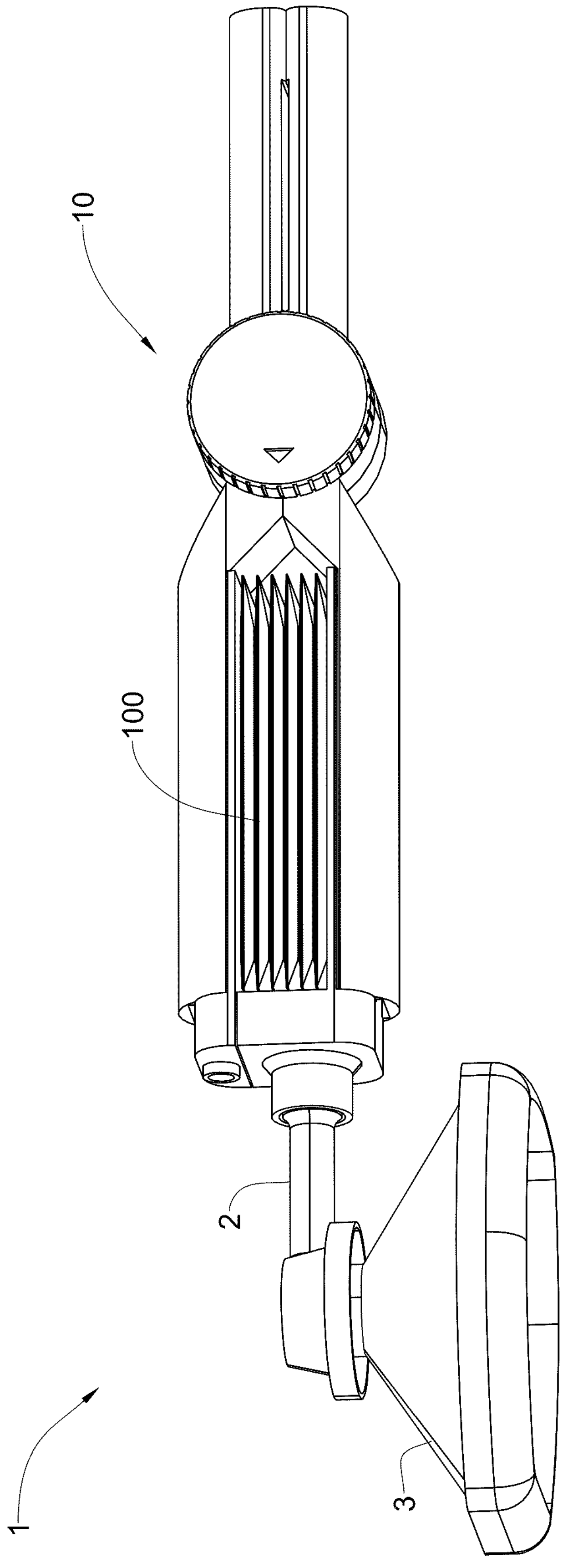
FIG. 1A is a perspective view of a kit comprising a respiratory support device and inflatable and deflatable cartridge according to an example of the presently disclosed subject matter in an assembled form along with an air tube and a mask.

Reference is made to FIG. 1A showing a kit 1 in accordance with a non-limiting example of the presently disclosed subject matter. According to the example shown in FIG. 1A, the kit 1 includes an air tube 2, a mask 3, a respiratory support device 10, and an inflatable and deflatable cartridge 100, shown in an assembled form in FIG. 1A. In the assembled form, the inflatable and deflatable cartridge 100 is operatively positioned into and attached to the respiratory support device 10 such that the respiratory support device 10 is operable to selectively inflate and deflate the cartridge 100. When the cartridge 100 is inflated, it inhales air from environment via an inlet opening and when the cartridge 100 is deflated, it exhales the air from an outlet opening. The air tube 2 connects the cartridge 100 to the mask 3 to deliver the exhaled air from the cartridge 100 to the mask 3 and eventually to the lungs of a patient. In some examples, the inlet opening can be connected to an oxygen cylinder and the cartridge can thus inhale oxygen therefrom and deliver the same to the patient in a similar manner as described above for the air from the environment. The operation of the respiratory support device 10 and the inflatable and deflatable cartridge 100 is described below with reference to FIGS. 1B to 1D, FIGS. 2A to 2E, and FIGS. 3A to 3D.

Figure 1B:
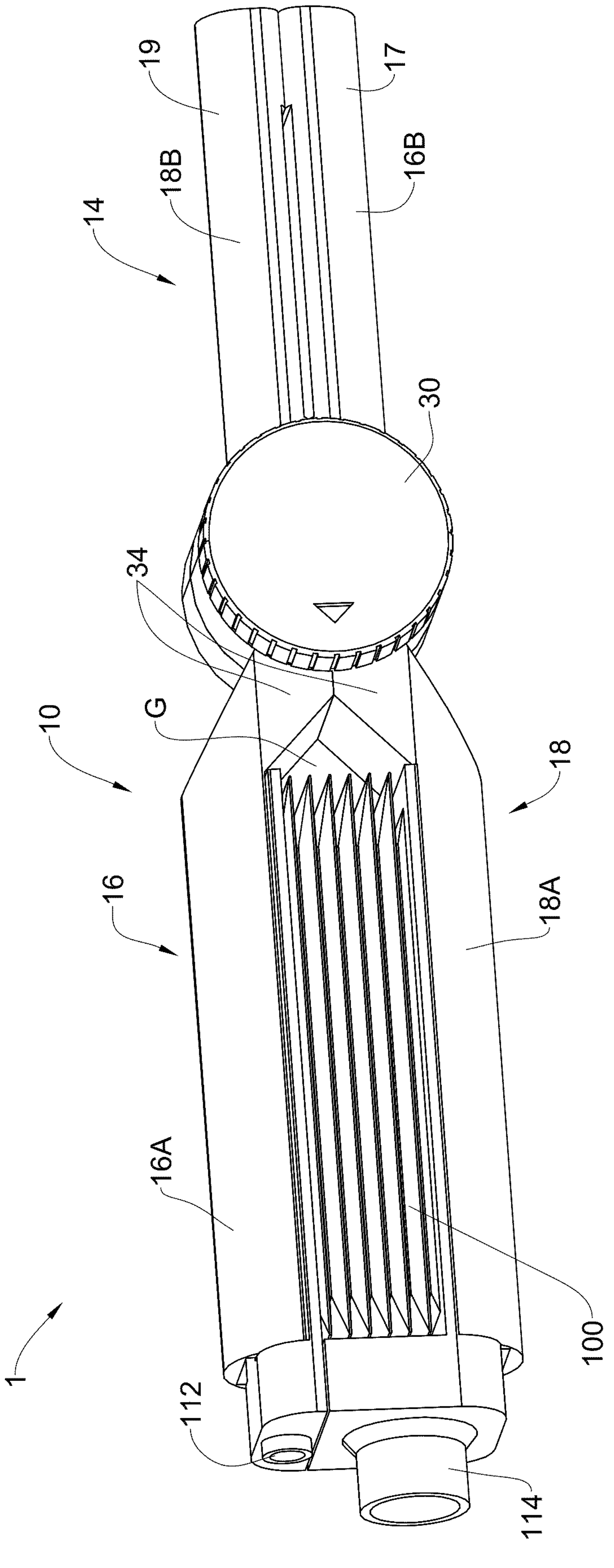
FIG. 1B is another perspective view of the kit of FIG. 1A according to another example of the presently disclosed subject matter without the air tube and the mask.
Figure 1C:
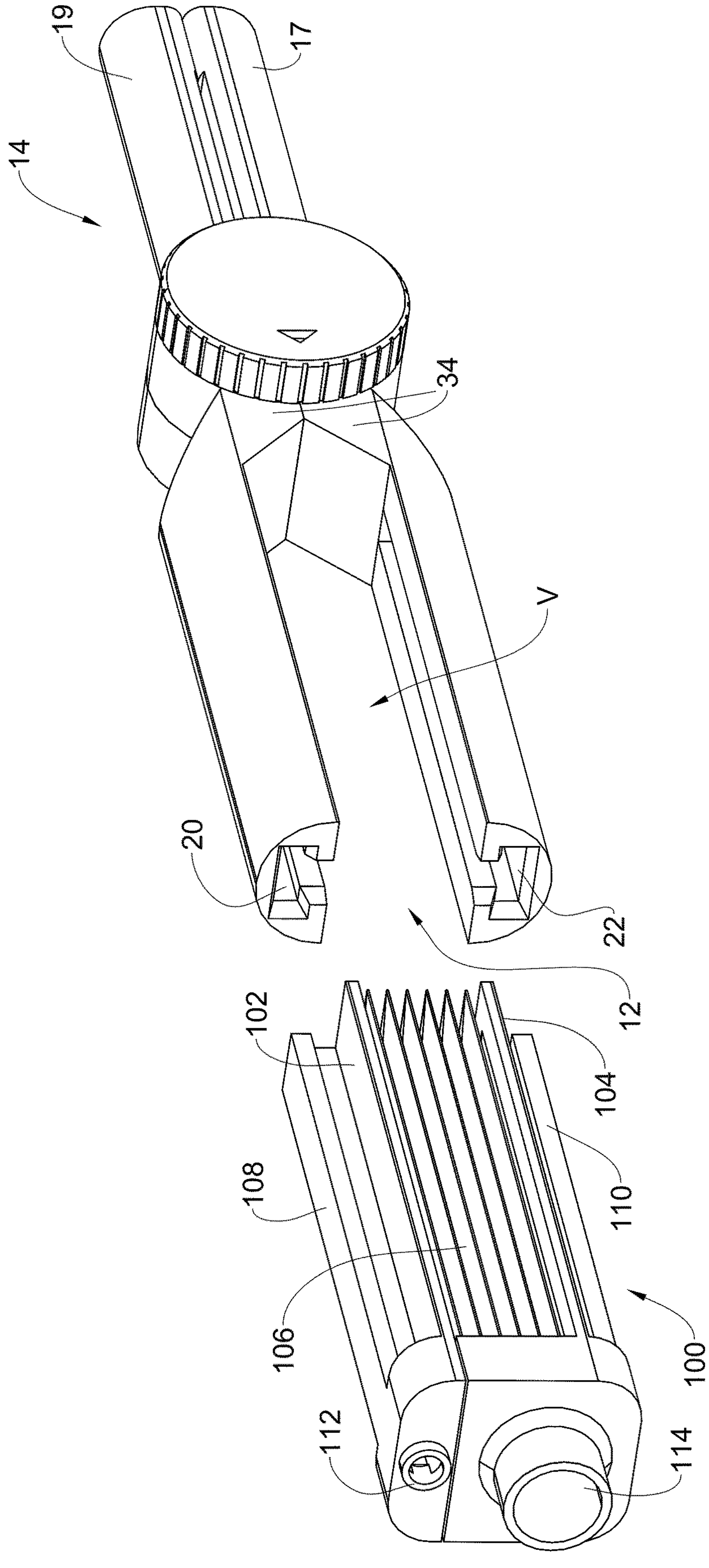
FIG. 1C is an exploded perspective view of the kit of FIG. 1B showing the kit in a disassembled form.
Figure 1D:
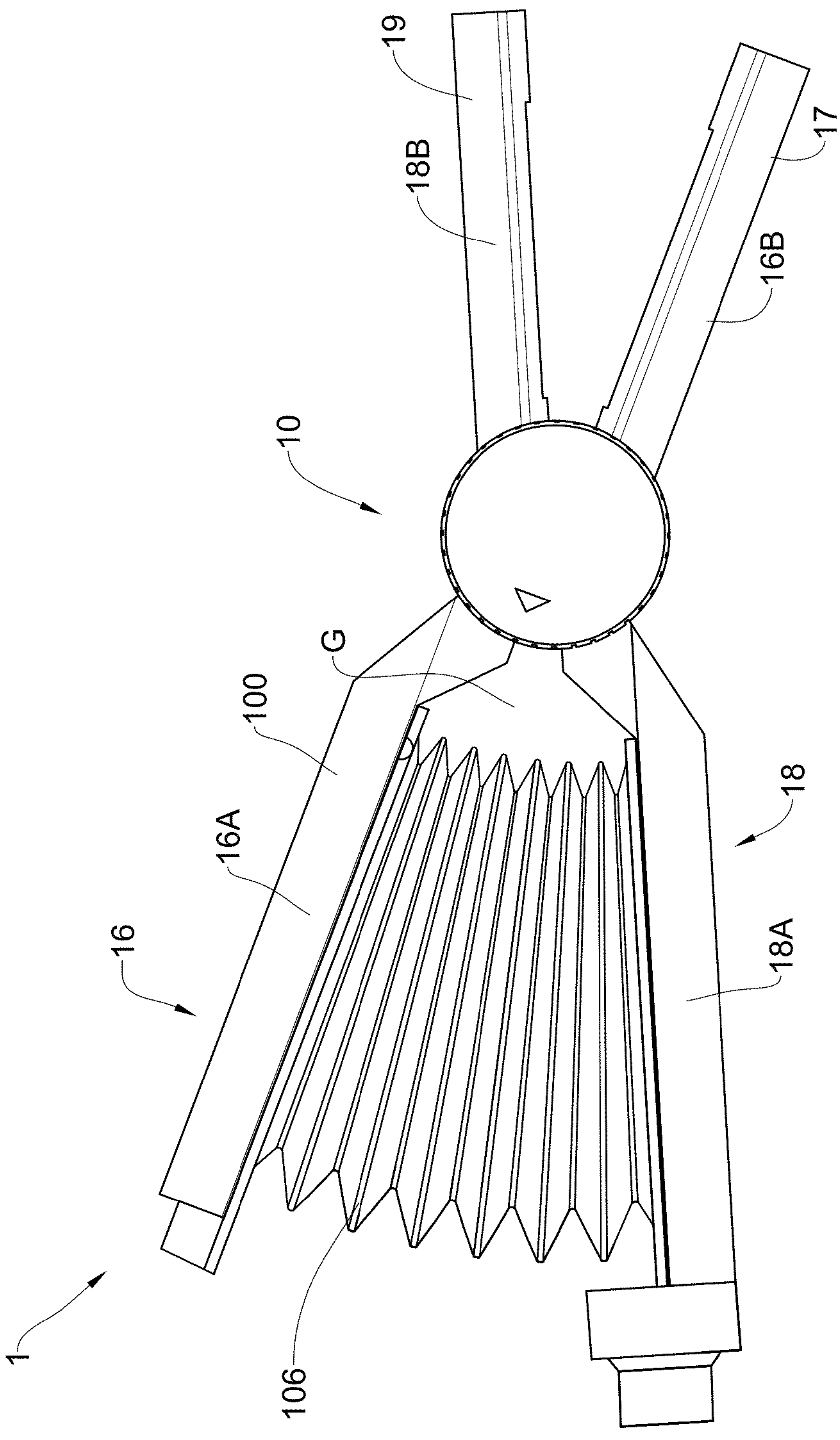
FIG. 1D is a side view of the kit of FIG. 1B showing the respiratory support device in an open state.

The kit 1, according to another example may not include the air tube 2 and the mask 2 and can be constituted by the respiratory support device 10 and the inflatable and deflatable cartridge 100. One such example is shown in FIGS. 1B to 1D.

Reference is now made to FIGS. 1B to 1D and FIGS. 2A to 2E in order to describe the structure and operation of the respiratory support device 10. The respiratory support device 10 is configured for use with an inflatable and deflatable cartridge, for example the inflatable and deflatable cartridge 100. The respiratory support device comprises a cartridge receiving portion 12 configured for removably attaching to the inflatable and deflatable cartridge and an actuating mechanism 14 configured for selectively inflating and deflating the inflatable and deflatable cartridge, when received in the cartridge receiving portion 12. The cartridge receiving portion 12 defines a volume V configured to contain an inflatable and deflatable portion of the inflatable and deflatable cartridge. The inflatable and deflatable portion can be an inflatable and deflatable bag constituting a part of the cartridge, as will be described later herein below. The volume V is configured to be expanded and contracted by means of the actuating mechanism 14.

In general, the respiratory support device can comprise a first arm and a second arm defining therebetween the cartridge receiving portion, thereby also defining the volume V therebetween. The first and the second arms can have respective first and second receptacles, each configured to removably engage a corresponding catcher of the inflatable and deflatable cartridge to attach the cartridge to the cartridge receiving portion.

According to a first example (not shown), the first and second arms may be free of any direct connections with each other, and can be independently operated by a user to change a distance therebetween, thereby expanding or contracting the volume defined by the cartridge receiving portion. In this case, almost whole of the length of the arms can constitute the cartridge receiving portion, and portions thereof configured to be held (for example by handles positioned thereon) by the user for the above-mentioned operation thereby constituting the actuating mechanism.

According to a second example (not shown), the first and the second arms can be pivotally connected to each other at one of their ends (for example, distal ends) thereof, and the opposite ends (for example, proximal ends) can be held by a user to pivot the arms with respect to each other to change a distance between the arms, thereby expanding or contracting the volume defined by the cartridge receiving portion. In this case, portions of the arms adjacent the connection/pivotal point (i.e., distal portions) can constitute the cartridge receiving portion, and portions of the arms distant from the connection/pivotal point (i.e., proximal portions) can be configured to be held by the user for the above-mentioned operation thereby constituting the actuating mechanism.

According to a third example (illustrated herein), the first and second arms can be pivotally connected to each other at a central portion extending between their proximal and distal ends. It is to be understood that the central portions may or may not be at exactly middle of the arms. The distal portions (for example, the portions extending between the distal end and the connection point) can constitute the cartridge receiving portion and the proximal portions (for example, the portions extending between the proximal end and the connection point) can be held by a user to pivot the arms with respect to each other to change a distance between the distal portions of the arms, thereby expanding or contracting the volume defined by the cartridge receiving portion. The proximal portions can thus constitute the actuating mechanism. In this example, the arms have been illustrated as crossing each other at the central portions, and the respiratory support device forms an X-like structure, and more particularly a plier-like structure.

According to the third example of the respiratory support device, as shown in FIGS. 1B to 1D and FIGS. 2A to 2E, the first and second arms extend along a device longitudinal axis DLA, and have been designated as 16 and 18 respectively. The first arm 16 has the first distal portion 16A, the first proximal portion 16B, and the first central portion 16C extending therebetween. The second arm 18 has the second distal portion 18A, the second proximal portion 18B, and the second central portion 18C extending therebetween. The arms 16 and 18 are pivotally connected to each at other at the central portions 16C and 18C. The distal portions 16A and 18A define therebetween the cartridge receiving portion 12 defining the volume V. The proximal portions 16B and 18B include handles 17 and 19 respectively configured to be held by a user to pivot the arms 16 and 18 with respect to each other about a pivot axis PA. Thus, the handles 17 and 19, or in fact the proximal portions 16B and 18B, constitute a part of the actuating mechanism 14.

The first distal portion 16A comprises the first receptacle 20 facing the second arm 18, or in fact the second distal portion 18A, and the second distal portion 18A comprises the second receptacle 22 facing the first arm 18, or in fact the first distal portion 16A. The first and second receptacles 20 and 22 define the cartridge receiving portion 12 and include the volume V therebetween. As is clear at least from FIGS. 1B and 1C, each of the receptacles 20 and 22 is configured to removably engage a corresponding catcher of the cartridge to thereby attach the cartridge to the cartridge receiving portion 12. The receptacles 20 and 22, each being an elongated receptacle extending along the device longitudinal axis DLA and, in the illustrated example, being formed as a single T-shaped element elongated so as to extend along a length DL of the cartridge receiving portion 12. In some examples, one or both of the receptacles 20 and 22 can be formed by discrete receptacles positioned on the respective arm along the length DL separated from each other. Also, in some examples, the cross-sectional shape, which in the illustrated example is T-shaped, can be any other suitable shape including circular, oval, semicircular, etc. Although in the illustrated example, the receptacles have been shown to be formed as recesses in the respective arms, it is to be understood that in some examples, the receptacles can be formed as protrusions protruding towards each other from the respective arms and configured to engage corresponding catchers of the cartridge, which in such examples can be formed as recesses. The receptacles being formed as elongated elements also constitute guides for the catchers during insertion of the cartridge into the cartridge receiving portion, thereby facilitating a proper positioning of the cartridge in the cartridge receiving portion.

As can be seen in the figures, the receptacles 20 and 22 extend along almost whole of the length DL of the cartridge receiving portion 12. In some examples, the receptacles 20 and 22 can extend along a length lesser than whole of, but extend along at least a majority of, the length DL of the cartridge receiving portion 12. The length RL of the receptacles 20 and 22 corresponds to a length of the corresponding catchers of the cartridge. The lengths RL of the receptacles 20 and 22 extending along a majority of length DL as well as corresponding to the length of the catchers ensure a gripping of the cartridge along a majority of its length, thereby ensuring a more efficient operation of the cartridge and the respiratory support device, as will be described later herein below. Also, the receptacles 20 and 22 are aligned in a plane extending along the device longitudinal axis DLA, which in the illustrated example is the plane of the paper.

Figure 2A:
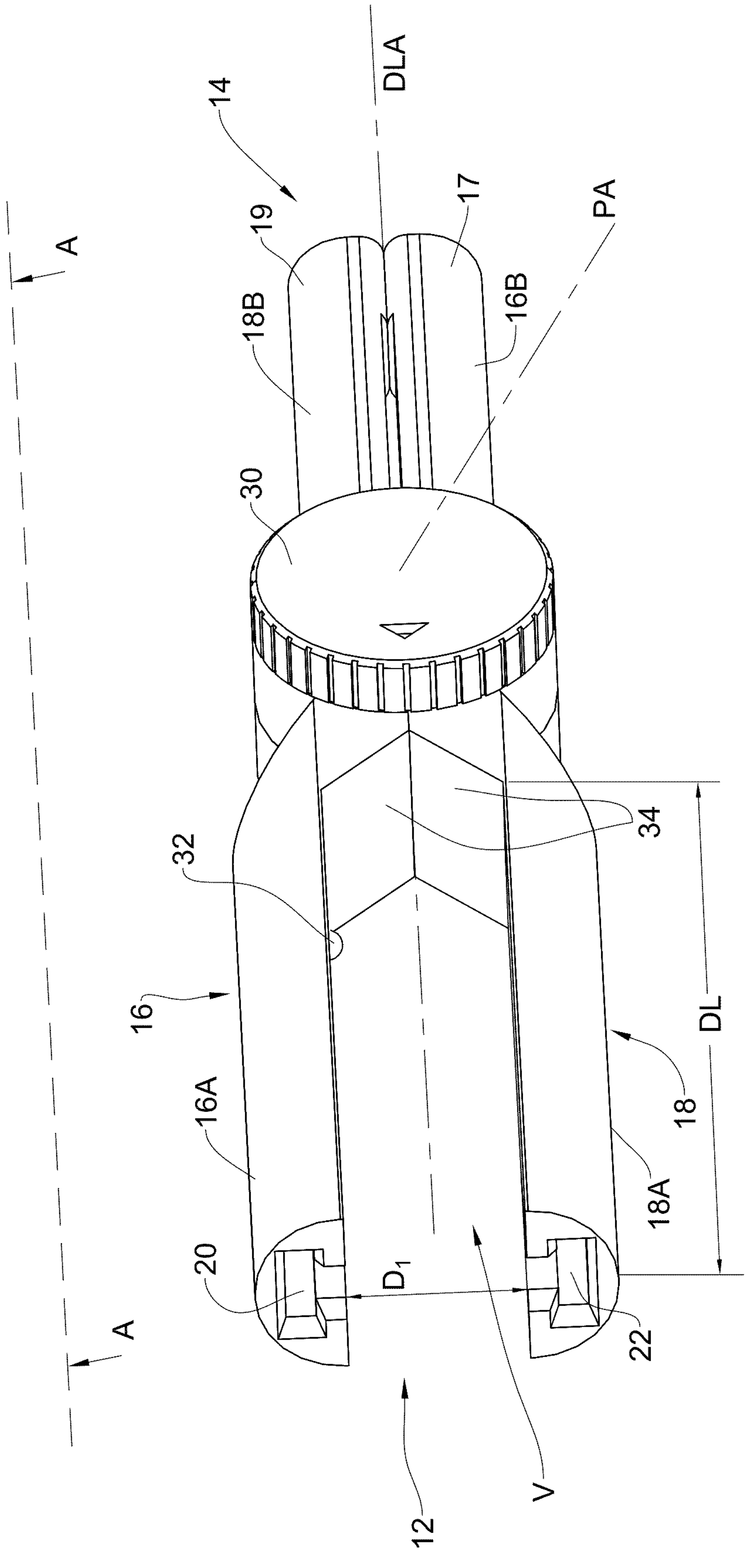
FIG. 2A is a perspective view of a respiratory support device according to an example of the presently disclosed subject matter in a closed state.
Figure 2B:
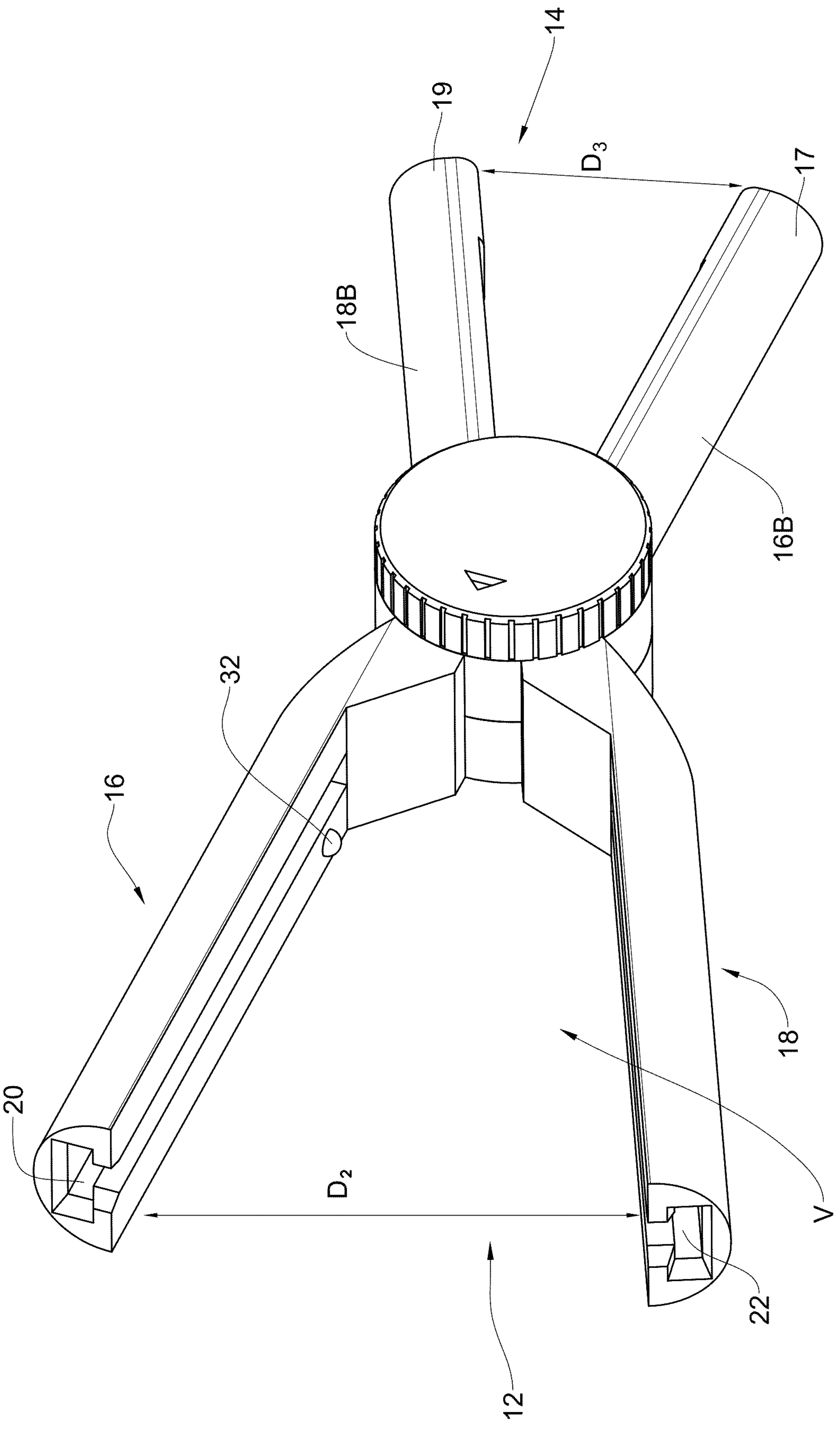
FIG. 2B is a perspective view of the respiratory support device of FIG. 2A in an open state.
Figure 2C:
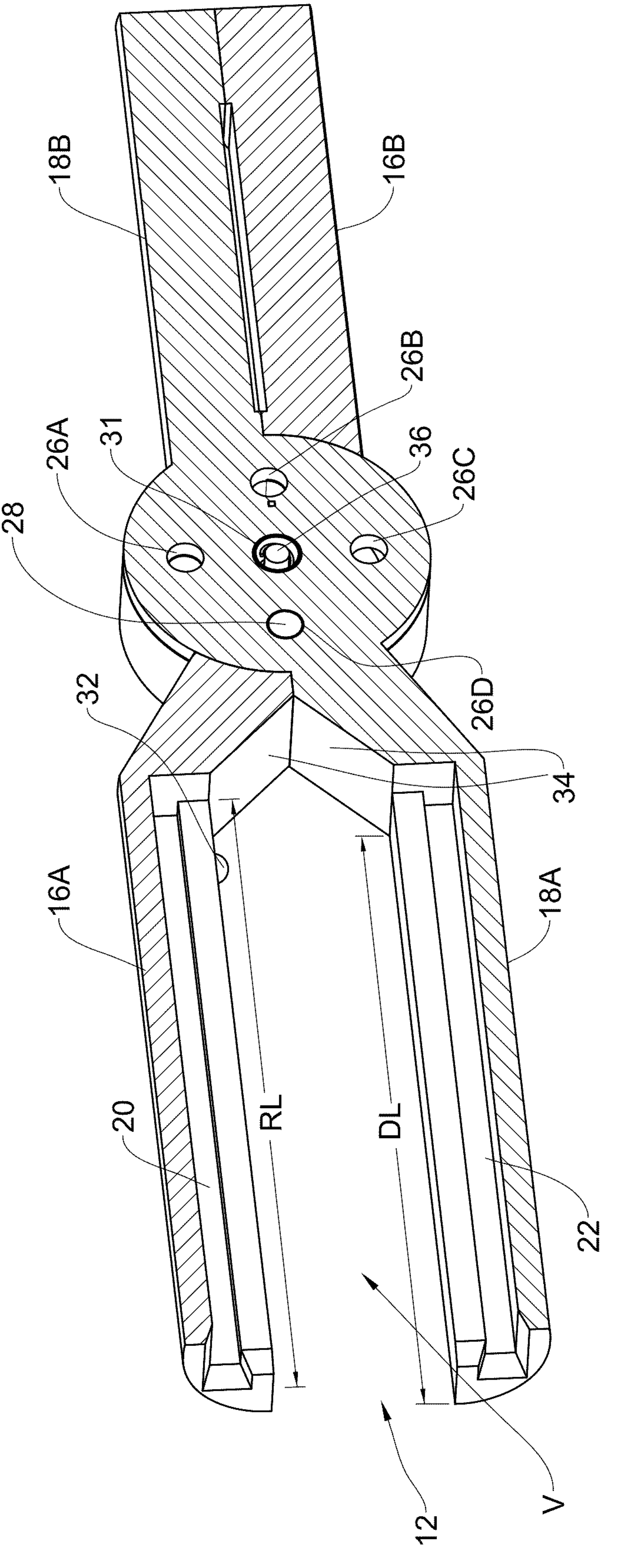
FIG. 2C is a cross-sectional view of the respiratory support device of FIG. 2A, along line A-A in FIG. 2A.
Figure 2D:
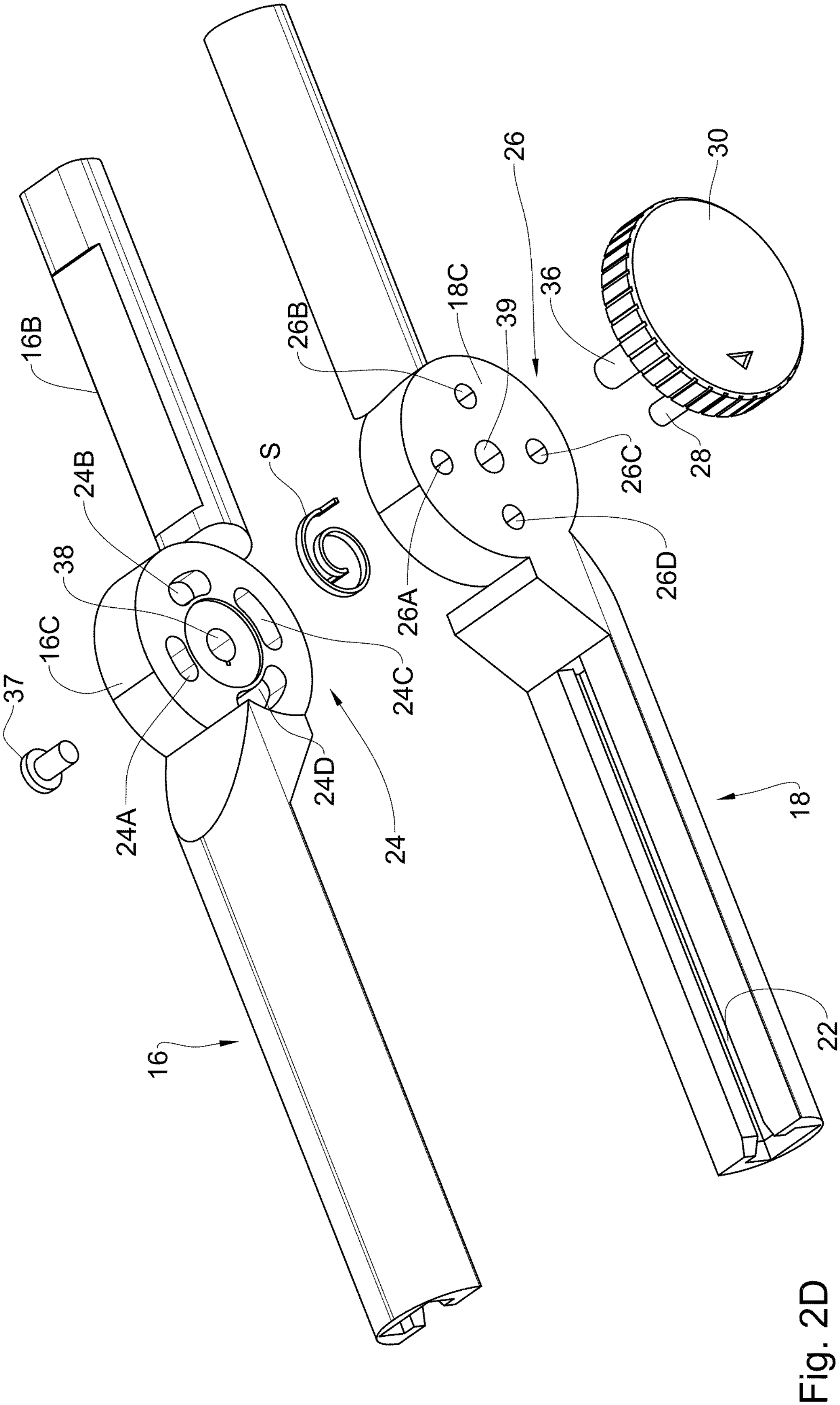
FIG. 2D is an exploded perspective view of the respiratory support device of FIG. 2A.
Figure 2E:
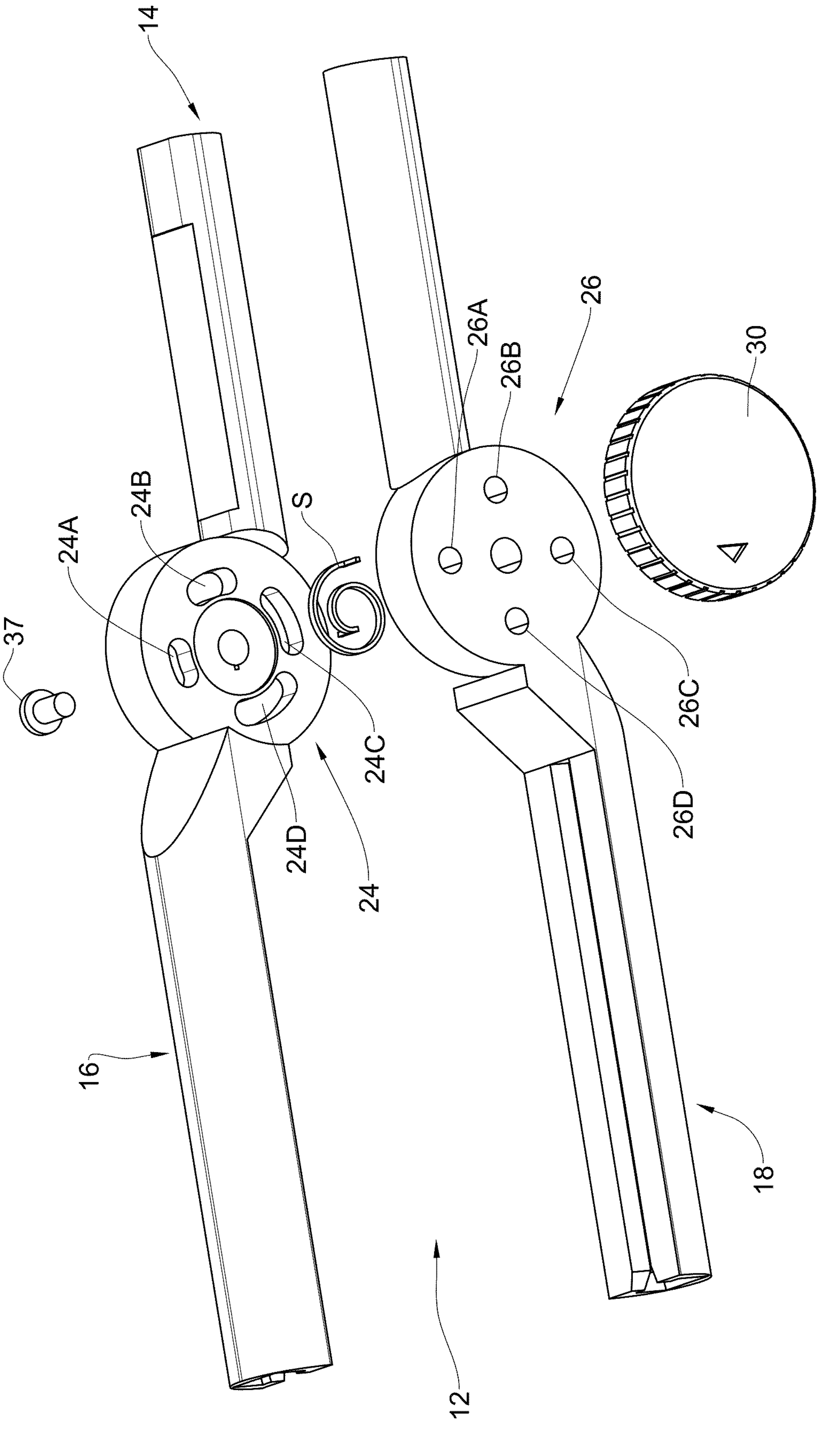
FIG. 2E is another exploded perspective view of the respiratory support device of FIG. 2A.

The actuating mechanism 14 is configured to be operated by the user to displace the respiratory support device 10 between a closed state, shown in FIGS. 1B, 1C, 2A, 2C, 2D, and 2E, and an open state, shown in FIGS. 1D and 2B.

In general (according to all the three examples of the respiratory support device described above), in the closed state of the respiratory support device, the portions of the arms defining the cartridge receiving portions can be at a first maximal distance from each other, and at the open state, those portions can be at a second maximal distance, greater than the first maximal distance, from each other. Thus, the volume V is expanded at the open state of the device and is contracted at the closed state thereof. When the cartridge is positioned in the cartridge receiving portion, the cartridge is inflated when the device is at its open state and is deflated when the device is in its closed state. In other words, expanding the volume V causes the cartridge to inflate (or to switch into its inflated state) and contracting the cartridge causes the cartridge to deflate (or to switch into its deflated state).

In the illustrated example, at the closed state of the device 10, the distal ends of the distal portions 16A and 18A are at the first maximal distance D1 from each other. At this state, the handles 17 and 19, constituting the actuating mechanism, are positioned close to each other enough to at least partially (i.e., at some portions, as shown) abut each other. In some examples, at the closed state, the handles may not abut each other and can be disposed at a minimum distance from each other. At the open state, the distal ends of the distal portions 16A and 18A are at the second maximal distance D2, greater than D1, from each other. At this state, the handles 17 and 19 are separated by a third maximal distance D3 between the proximal ends thereof. The handles 17 and 19, constituting the actuating mechanism in the illustrated example, can be held by a user to pivot the arms 16 and 18 with respect to each other to selectively increase and decrease the maximal distance between the distal ends, to thereby respectively expand and contract the volume V, to further thereby respectively inflate and deflate the cartridge (when positioned in the cartridge receiving portion).

In general, the device can include a biasing element configured to bias, and thus to maintain, the device into its open state (when no external force is applied thereto). The actuating mechanism can thus be operated by a user to displace the device into its closed state by application of a force on the actuating mechanism against the bias of the biasing element. In response to withdrawal of said force, the biasing element again automatically displaces the device into its open state. It is to be understood herein that the actuating mechanism can thus be operated by simply pressing the actuating mechanism against the bias of the biasing element, which then automatically displaces into its open state, and thus, the device can be operated by multiple pressing forces. Therefore, if in the open state of the device, the maximal distance between the portions of the arms constituting the actuating mechanism corresponds to size of one hand of a normal human being, the device can be held and operated by a single hand by the user, by repeatedly pressing the actuating mechanism. For instance, in the open state, the maximal distance (or the distance at that portion that is to be held by the user for the above-mentioned operation) between the portions of the arms constituting the actuating mechanism can be approximately 10-20 cm, more particularly 12-18 cm or 14-16 cm, in direction perpendicular to the device longitudinal axis DLA so as to be held by one hand of the user.

In the illustrated example, the biasing element is a spring S positioned at the point of connection of the arms configured to bias the device 10 into is open state. The handles 17 and 19 can be pressed towards each other against the bias of the spring S to displace the device into its closed position. Once the pressing force is withdrawn, the spring S biases the device 10 into its open state, which can then be closed again by the pressing force for repeated operation. In the open state, the maximal distance D3 is such that the handles 17 and 19 can be held by a single hand of the user to apply the above-mentioned pressing force against the bias of the spring S for an easy and repeated operation of the device 10 by a single hand of the user. In some examples, the device can include a fastening mechanism (not shown) configured to hold the device 10 in its closed state for storage and transportation purposes.

As can be seen in the illustrated example (best seen in FIG. 1C), the receptacles 20 and 22 extend parallel to each other in the closed state of the device 10, thereby being configured to slidingly engage with the corresponding catchers of the cartridge when the cartridge is slid into the cartridge receiving portion 12 along the device longitudinal axis DLA. Thus, in the illustrated example, the cartridge receiving portion is configured to receive therein the cartridge when the cartridge is in its deflated state and the device 10 is in its closed state. At this state, the cartridge can be slid into the cartridge receiving portion 12 along the device longitudinal axis DLA while slidingly engaging the catchers with the receptacles 20 and 22.

Further, in general (according to all the three examples of the respiratory support device described above), the respiratory support device can include a limiter configured to limit an extent of expansion and/or contraction of the volume V upon operation of the actuating mechanism. The extent of expansion/contraction of the volume V defines the amount of air inhaled and exhaled by the cartridge when positioned in the respiratory support device, and thus, needs to be limited according to amount of air to be delivered to a patient in one operation cycle of the actuating mechanism (i.e, one inflation and deflation of the cartridge). Also, the respiratory support device can include a selection mechanism to facilitate a user to select the extent among a plurality of operations. For instance, a single device can then be used to provide respiratory support to different patients requiring (as per prescription) different volumes of air to be delivered at once, i.e., with a single operation of the actuating mechanism.

In the illustrated example, the limiter has been designated as 24 and the selection mechanism has been designated as 26. The limiter 24 and the selection mechanism 26 operate in correspondence with each other whereas the limiter 24 comprises four arch shaped slots 24A, 24B, 24C, and 24D formed in the central portion 16C of the first arm 16. The selection mechanism 26 comprises a selection pin 28 protruding from an interior surface 30A of a knob 30. The selection mechanism 26 further comprises four holes 26A, 26B, 26C, and 26D, formed in the central portion 18C of the second arm 18, each corresponding to, and aligned with, a respective one of the slots 24A—24D. The selection pin 28 can be positioned in one of the slots 24A—24D through the corresponding one of the holes 26A—26D. The four slots 24A—24D, each have a different arch length about the pivot axis PA determining the extent of a distance to which the selection pin 28 can move within the slot. The pivoting of the arms 16 and 18 causes the selection pin 28 (being positioned through one of the holes 26A—26D formed in the second arm 18) to move within the slot in which the selection pin 28 is positioned. The length of the slot about the pivot axis PA limits the extent of pivoting of the arms 16 and 18, thereby limiting the extent of the expansion of volume V. The knob 30 can be pulled outwardly along the pivot axis PA to such an extent that the selection pin 28 is released from the holes 26A—26D. Then, the knob 30 can be rotated to align the selection pin 28 with any desired hole and then can be pushed (either manually or by action of a spring 31, best seen in FIG. 2C) inwardly such that the selection pin 28 is positioned in the selected slot through the corresponding hole, thereby facilitating the selection of extent of expansion of the volume V among four options (each corresponding to a slot). In other examples, the limiter and the selection mechanism can be implemented in any other manner as would be understood to a person skilled in the art. Also, there can be more or less than four options for extent of expansion of volume V in any of such examples. In fact, the selection mechanism and the limiter can be configured to facilitate selection of extent of contraction of the volume V, instead of or in addition to the extent of expansion.

The respiratory support device 10 further includes a central pin 36 about which the two arms 16 and 18 pivot. The central pin protrudes inwardly from the knob 30 and is secured to a securing pin 37 from a side of the device 10 opposite to the knob 30. The securing pin 37 holds the central pin in place and thus the device 10 assembled during operation thereof. The first central portion 16C and the second central portion 18C include central holes 38 and 39 respectively through which the central pin 36 passes to be secured to the securing pin 37. The two arms 16 and 18 are thus pivotally connected to each other by the central pin 36 which also constitutes, or at least includes, the pivot axis PA.

In general, the respiratory support device 10 can further include a device locking element configured to removably lock a corresponding cartridge locking element of the cartridge when the cartridge is positioned in the cartridge receiving portion. The device locking element can be positioned anywhere in (or in proximity of) the cartridge receiving portion, and more particularly in, or in proximity to the receptacles.

In the illustrated example, the device locking element is a spring pin 32 positioned at the first arm 16 on a surface adjacent the receptacle 20 facing the second arm 18. The spring pin 32 is positioned within the cartridge receiving portion 12 and is configured to removably lock with the corresponding cartridge locking element, which in this case would be a locking recess corresponding in shape, size, and location to that of the spring pin 32. When the cartridge is inserted in the cartridge receiving portion 12, the spring pin 32 is pushed inwardly by the cartridge and when the locking recess aligns with the spring pin 32, during said insertion, the spring pin 32 falls into the locking recess by virtue of its spring action, thereby attaching the cartridge in the cartridge receiving portion. In some examples, the device locking element can be a locking recess and the cartridge locking element can be a spring pin.

For extraction of the cartridge, the spring pin 32 can be accessed, and pressed by a suitable tool (as simple as a thin pin) out of the locking recess, and the cartridge can be extracted from the cartridge receiving portion 12. Further, for an easy extraction of the cartridge from the cartridge receiving portion 12, the device 10, and especially the cartridge receiving portion 12 is sized and shaped such that to leave a gap G (best seen in FIG. 1B) between a proximal wall of the cartridge receiving portion 12 and the cartridge, when the cartridge is attached in the cartridge receiving portion 12. In the illustrated example, the proximal wall of the cartridge receiving portion 12 is constituted by a stopper 34, which is shaped in the form of a ‘V’ having a depth away from the cartridge receiving portion 12 thereby leaving the gap G between the stopper 34 and the cartridge for a user to insert a finger (or a tool) into the gap G to extract the cartridge from the cartridge receiving portion 12. In some examples, the gap G can be obtained by the proximal wall of the cartridge receiving portion having any other shape suitable for the above-mentioned purpose.

In the illustrated example, the stopper 34 not only form the gap G, but also prevents the distal portions 16A and 18A from abutting each other. In other words, the stopper 34 maintains the volume V at its minimum non-zero volume at the closed state of the device 10. The stopper 34 is sized and positioned such that at the closed state of the device 10, the receptacles 20 and 22 extend parallel to each other.

Although, the third example of the respiratory support device has been explained in detail, it is to be understood that the relevant description of the operation of the cartridge receiving portion, the receptacles, the actuation mechanism (apart from the pivoting of the arms, for the first example), the limiter, the selection mechanism, the biasing element, and the stopper applies analogously to the first and the second examples mentioned above of the respiratory support device, and this description with regard to the first and the second examples has not been repeated for the sake of conciseness of the present application.

Although all the examples of the respiratory support device have been described as being configured for use with a removable cartridge, it is to be understood that according to some other examples, the respiratory support device can have the same structure as illustrated herein, i.e., the cross-like (X-like), and more particularly the plier-like structure, and can operate as described herein, with the only difference that instead of a removable cartridge, the device (in those other examples) can be configured to operate with fixed inflatable and deflatable bags. In such examples, the receptacles can include, or even be replaced by, fixed connection elements configured to fixedly attach the inflatable and deflatable bag.

In all of the above examples, the actuating mechanism has been described as being fully manual, however, it is to be understood herein that in some examples, the actuating mechanism, in place of or in addition to the manually functional components, can include electrically and/or electronically operated actuator, such as a motor, configured to expand and contract the volume V defined by the cartridge receiving portion.

Reference is now made to FIGS. 1B to 1D and FIGS. 3A to 3D to describe in detail the structure and operation of the inflatable and deflatable cartridge 100. The cartridge 100 is configured to use with a respiratory support device, for example the respiratory support device 10, configured to attach to the cartridge and inflate and deflate the cartridge for providing respiratory support to a patient. The cartridge 100 is configured to be removably received in the respiratory support device, and to be selectively inflated and deflated by an actuating mechanism, for example the actuating mechanism 14, of the respiratory support device when received therein. The inflatable and deflatable cartridge 100 is configured to inhale air, from the environment or oxygen from an oxygen cylinder connected thereto, when inflated and exhale air (or the oxygen) when deflated.

In general, the cartridge 100 can comprise a first support base and a second support base configured to provide structural strength and stability to the inflatable and deflatable cartridge 100. The support bases can be positioned on two opposite sides of a cartridge longitudinal axis CA. In other words, the first support base is spaced from the second support base in a direction perpendicular to the cartridge longitudinal axis CA. The cartridge 100 can further comprise an inflatable and deflatable bag portion disposed between, and fixedly connected to, the two support bases. The inflatable and deflatable bag portion can be formed of a flexible material facilitating inflation and deflation of the inflatable and deflatable bag, whereas the support bases are formed of a rigid material suitable to provide structure support to the inflatable and deflatable bag portion. The support bases can extend along at least a majority of, more particularly whole of, a length of the inflatable and deflatable bag portion in a direction along the cartridge longitudinal axis. The support bases extending along a majority of, or whole of, the inflatable and deflatable bag portion provides the structural support thereto along its whole length. The inflatable and deflatable bag portion can be configured to be inflated by pulling at least one of the support bases away from the other one of the support bases, and to be deflated by pushing at least one of the support bases towards the other one of the support bases. For instance, the support bases can be held by a user and pulling them apart causes the inflation of the inflatable and deflatable bag portion and pushing them towards one another causes deflation of the inflatable and deflatable bag portion. Either of the support bases can be pulled away from, and pushed towards, the other of the support bases for inflating and deflating the bag portion. Also, both of support bases can be pulled away from and pushed towards each other to inflate and deflate the inflatable and deflatable bag portion.

Figure 3A:
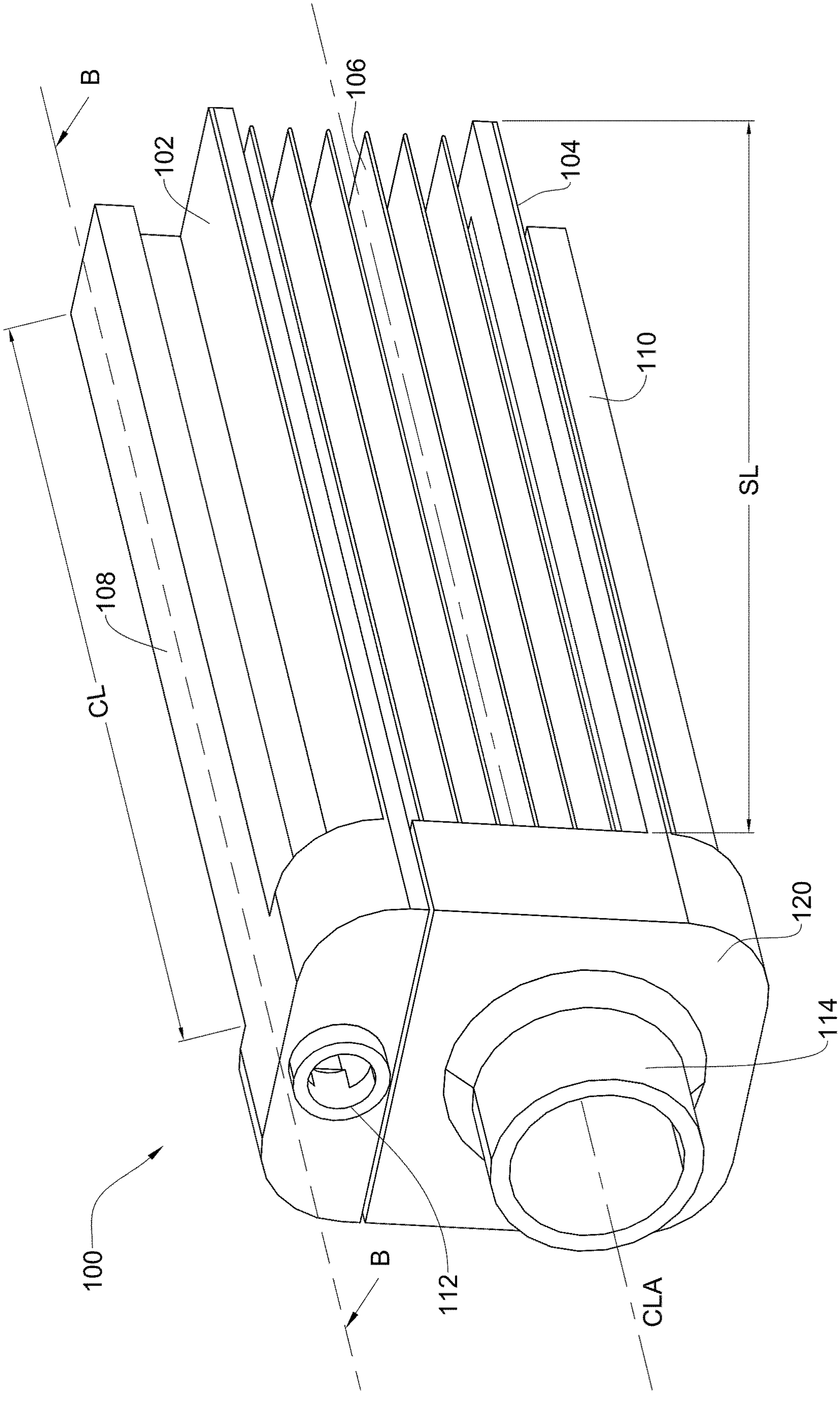
FIG. 3A is a perspective view of an inflatable and deflatable cartridge according to an example of the presently disclosed subject matter in a deflated state.
Figure 3B:
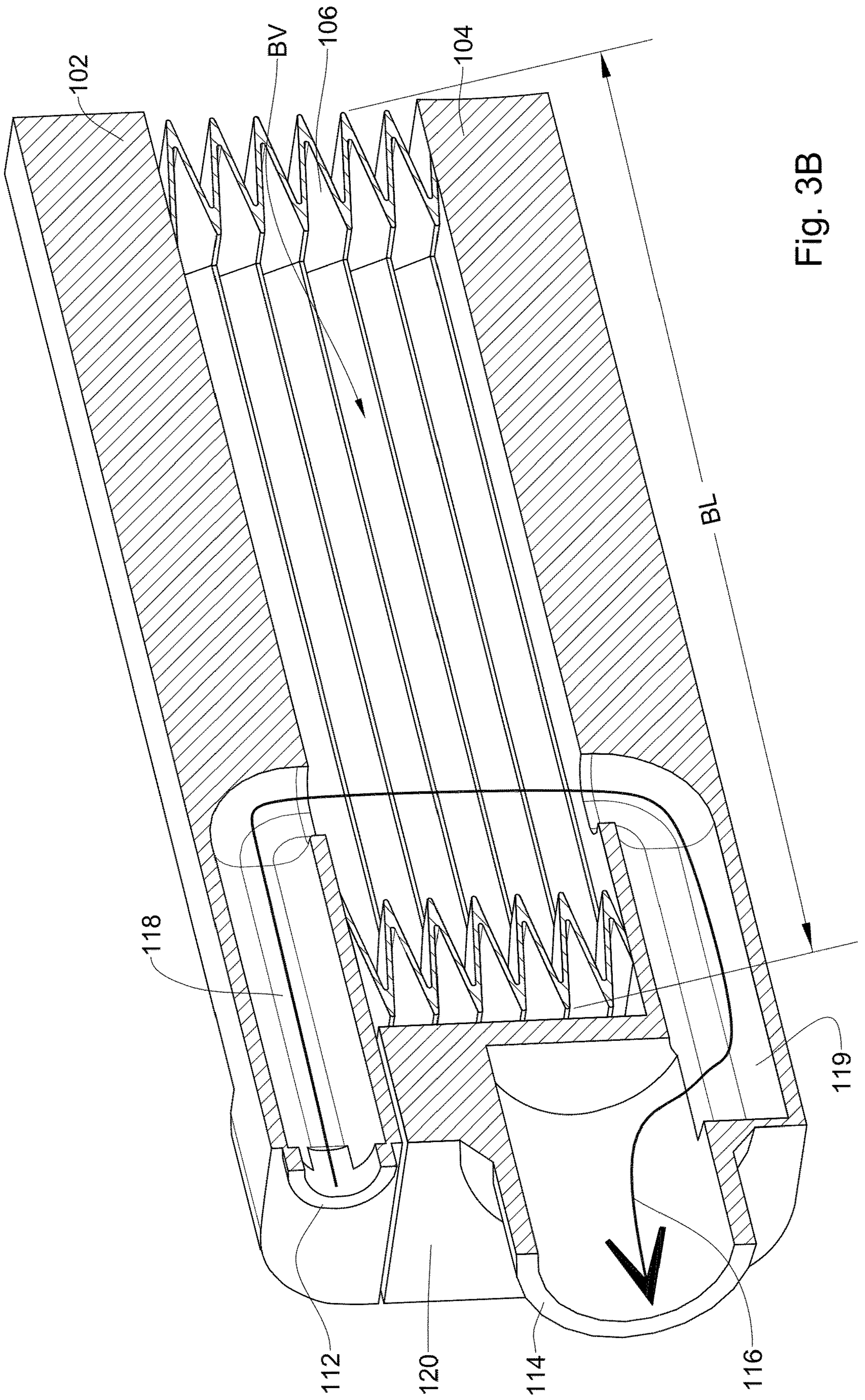
FIG. 3B is a cross-sectional view of the inflatable and deflatable cartridge of FIG. 3A, along line B-B in FIG. 3A.
Figure 3C:
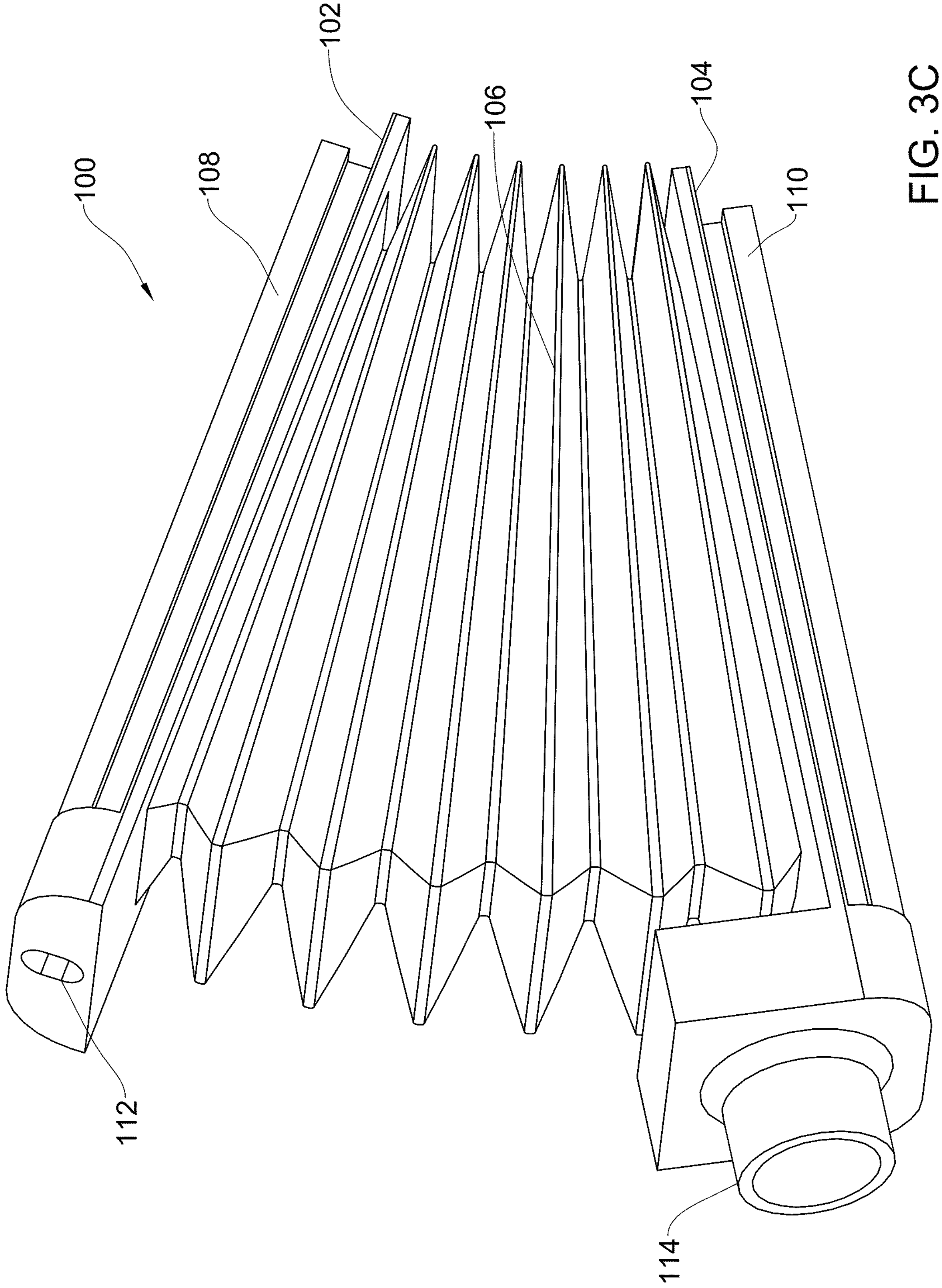
FIG. 3C is a perspective view of the inflatable and deflatable cartridge of FIG. 3A in an inflated state.
Figure 3D:
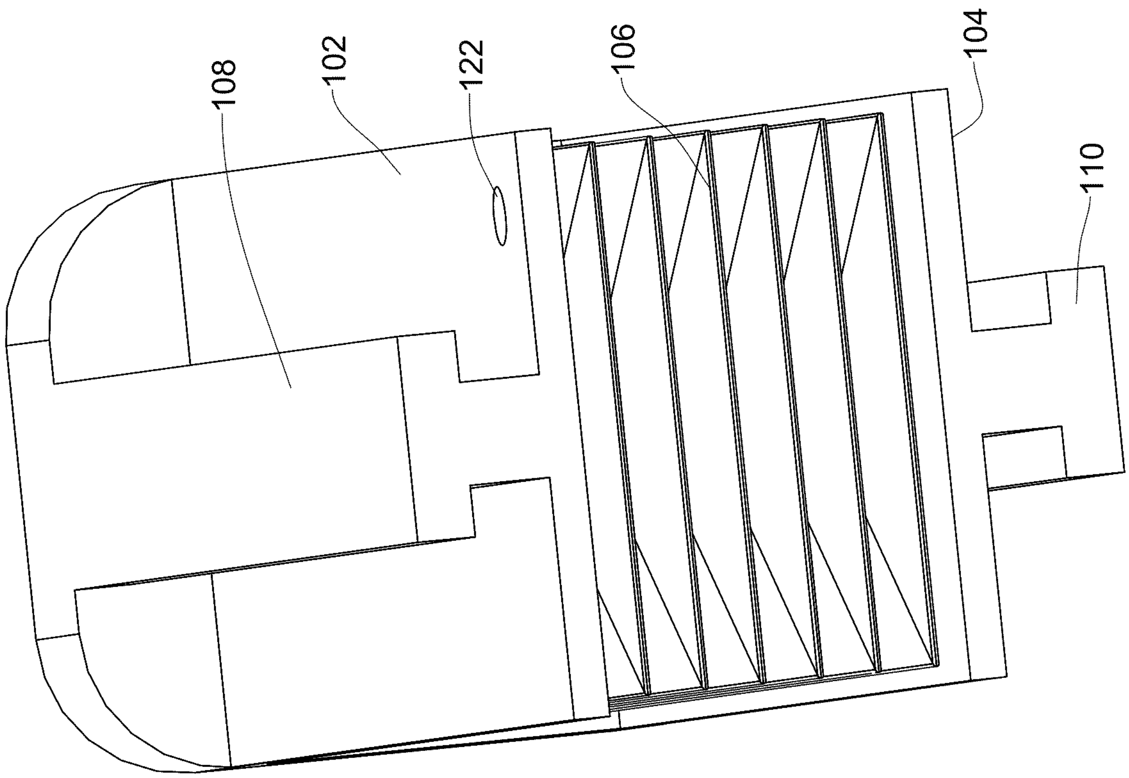
FIG. 3D is a rear perspective view of the inflatable and deflatable cartridge of FIG. 3A.

In the illustrated example, the first and the second support bases have been designated as 102 and 104 respectively, and the inflatable and deflatable bag portion has been designated as 106. As can be seen in FIGS. 3A to 3C, the support bases 102 and 104 extend along almost whole of the length BL of the inflatable and deflatable bag along the cartridge longitudinal axis CA. The cartridge 100, and particularly the inflatable and deflatable bag portion 106, can be displaced between a deflated state, as shown in FIGS. 1B, 1C, 3A, 3B, and 3D, and an inflated state, as shown in FIGS. 1D and 3C. the support bases 102 and 104 are configured to be held strongly and pushed and pulled to displace the inflatable and deflatable cartridge 100 between its deflated and inflated states. In the illustrated example, the cartridge 100 is an accordion-like structure, and the two support bases 102 and 104 extend parallel to each other in the deflated state of the cartridge 100. As is clear from FIG. 1C, the cartridge 100 is configured to be received in the respiratory support device in a deflated state, and when the respiratory support device is in its closed state, as described above with reference to the respiratory support device 10.

In general, for attaching the cartridge 100 to the respiratory support device, the cartridge can comprise catchers configured to engage corresponding receptacles, for example the receptacles 20 and 22, of the respiratory support device. The first support base can comprises a first catcher configured to removably engage with a corresponding first receptacle of the respiratory support device, and the second support base comprises a second catcher configured to be removably engage with a corresponding second receptacle of the respiratory support device. For instance, in the illustrated example, the first catcher 108 is formed on the first support base 102 and faces away from the inflatable and deflatable bag portion 106 and the second catcher 110 is formed on the second support base 104 and faces away from the inflatable and deflatable bag portion 106. The catchers 108 and 110, each being an elongated catcher extending along the cartridge longitudinal axis CLA and, in the illustrated example, being formed as a single T-shaped element elongated so as to extend along a length SL of the corresponding support base. In some examples, one or both of the catchers 20 and 22 can be formed by discrete catchers positioned on the respective support base along the length SL separated from each other. Also, in some examples, the cross-sectional shape, which in the illustrated example is T-shaped, can be any other suitable shape including circular, oval, semicircular, etc. Although in the illustrated example, the catchers have been shown to be formed as protrusions protruding from the support bases, it is to be understood that in some examples, the catchers can be formed as recesses in the respective support bases and configured to engage corresponding receptacles of the respiratory support device, which in such examples can be formed as protrusions to be received in the recesses. The catchers being formed as elongated elements also constitute guides during insertion of the cartridge into the cartridge receiving portion of the respiratory support device, thereby facilitating a proper positioning of the cartridge.

As can be seen in the figures, the catchers 108 and 110 extend along almost whole of the length SL of the support bases 102 and 104. In some examples, the catchers 108 and 110 can extend along a length lesser than whole of, but extend along at least a majority of, the length SL of the support bases 102 and 104. The length CL of the catchers 108 and 110 corresponds to a length of the corresponding receptacle of the respiratory support device. The lengths CL of the catchers 108 and 110 extending along a majority of length SL as well as corresponding to the length of the receptacles ensure a gripping of the cartridge along a majority of its length, thereby ensuring a more efficient operation of the cartridge and the respiratory support device.

The features related to lengths, that whole or majority of length of the bag portion is covered by the support bases, the catchers extend along whole or majority of the lengths of the support bases, and that the lengths of the catchers and the receptacles correspond to each other facilitates an efficient inflation and deflation of the bag portion thereby consuming whole of the bag interior volume. This results in more efficient respiratory support with minimal force, as with a definite amount of the force, the whole of the bag interior volume is utilized, as compared to what would have been utilized in case the bag portion were not to be held throughout its length. Furthermore, these features ensure better support and holding strength for the cartridge in the respiratory support device. Therefore, in the context of the present application, the terms whole or, and majority of, are to understood as necessary as well as enough to serve the above-mentioned purposes. For instance, the term almost whole of the length is to be understood herein as the minimum length that would sufficiently serve the above-mentioned purpose and can be 90-100%, 80-90%, 70-80%, 60-70%, or 51-60% of the length that it corresponds to.

It is to be understood herein that the term parallel and/or substantially parallel when used in relation to the portions of the arms and receptacles of the respiratory support device and support bases and catchers of the cartridge intends to mean that these elements are parallel at least enough, if not absolutely parallel, to facilitate sliding insertion of the cartridge into the cartridge receiving portion and sliding engagement of the catchers with the cartridge. In some implementations, these elements may not be exactly parallel but can still allow the sliding insertion of the cartridge/catchers with respect to the cartridge receiving portion/receptacles, an such implementations are to be understood as falling within the spirit and scope of the term parallel. In other words, the term parallel is not limited to absolutely zero angle between these elements, and this be considered that a practical tolerance falls within the scope of the term parallel.

The cartridge 100 further comprises an inlet opening 112, an outlet opening 114, and an air flow path 116 extending between and including the inlet and the outlet openings 112 and 114. The inlet and the outlet openings 112 and 114 are in fluid communication with a bag interior volume BV defined by the inflatable and deflatable bag portion 106. The air flow path 116 extends through the interior bag volume BV so as to deliver the air inhaled by the inflatable and deflatable bag portion 106 via the inlet opening 112 to the outlet opening 114 to be exhaled therethrough. The cartridge 100, and more particularly the inflatable and deflatable bag portion 106 is configured to inhale the air through the inlet opening 112 when the cartridge 100 is inflated and to exhale the air through the outlet opening 114 when the cartridge 100 is deflated.

In general, the inlet and the outlet openings can be positioned anywhere at the cartridge 100 so as to be most suitable for connection thereof to an air tube, for example the air tube 2, to be connected the outlet opening 114 to deliver the exhaled air therethrough. In the illustrated example, the inlet and the outlet openings 112 and 114, both are positioned at a frontal side (the side that would face the patient during use) of the cartridge 100, and face away from the respiratory support device when received therein. The inlet and outlet openings 112 and 114 are positioned so as to be distant from any part of the respiratory support device to ensure sterility of the air being delivered to the patient. For instance, the air entering into the bag portion 106 through the inlet opening 112, and then being delivered through the air flow path 116 and the outlet opening 114 does not come in contact with any part of the respiratory support device, or in words, the inlet opening 112, the outlet opening 114, and the air flow path 116 are fluidly isolated from the respiratory support device during operation. This ensures the sterility of the air being delivered to the patient, especially and more particularly when the air is being delivered from an air source such as oxygen cylinder. Thus, the air does not come in contact with any part that might involve contact with the user.

As can be best seen in FIG. 3B, the inlet opening 112 is formed in a frontal end of the first support base 102 and an interior 118 of the support base 102 constitutes a part of the air flow path 116. Also, the air flow path 116 extends through an interior 119 of the second support base 104. In the illustrated example, the cartridge 100 comprises an opening base 120 and the outlet opening 114 is formed in the opening base 120. The opening base 120 is firmly articulated to the second support base 104, or in some examples the opening base 120 can be integrally formed with the second support base 104. In some other examples, the outlet opening 114 can be directly formed on a frontal end of the second support base 104. The openings 112 and 114 being formed on the rigid support bases 102 and 104, or on a rigid opening base 120, provides rigidity to the openings to be thereby connected stably to air tubes for inhaling and/or exhaling air, for example the air tube 2 for exhaling air therethrough. A stable connection at the openings ensure no disconnections and/or leakage at the openings during operation. Also, in some examples, the second support base 104 is configured to remain stationary during inflation and deflation of the cartridge 100 and the first support base 102 can be pulled away from and pushed towards the second support base 104 to inflate and deflate the cartridge 100. This further ensures a stable connection between the air tube and the outlet opening 114.

In general, the cartridge 100 can further include a cartridge locking element configured to removably lock a corresponding device locking element of the respiratory support device when the cartridge is positioned in the respiratory support device to thereby firmly hold the cartridge in the respiratory support device at least during operation thereof. The cartridge locking element can be positioned anywhere in (or in proximity of) any of the support bases, or at any of the catchers.

In the illustrated example, the cartridge locking element is a locking recess 122 positioned at the first support base 102 on a surface adjacent the catcher 108 that would face an arm, for example the first arm 16 in the illustrated examples, of the respiratory support device. The locking recess 122 is configured to removably lock with the corresponding device locking element, which in this case would be a spring pin, for example the spring pin 32, corresponding in shape, size, and location (at the respiratory support device) to that of the locking recess 122. In some examples, the cartridge locking element can be a spring pin and the device locking element can be a locking recess.

The invention claimed is:

1. A respiratory support device for use with an inflatable and deflatable cartridge, said device comprising:

a cartridge receiving portion for removably attaching to the inflatable and deflatable cartridge;

an actuating mechanism configured for selectively inflating and deflating the inflatable and deflatable cartridge, when received in the cartridge receiving portion; and a first arm and a second arm defining at least partially said cartridge receiving portion therebetween;

the first arm comprising a first receptacle facing the second arm, and the second arm comprising a second receptacle facing the first arm, the first and the second receptacles defining at least partially the cartridge receiving portion:

wherein each of the first and the second receptacles is configured to removably engage a corresponding one of a first and a second catcher of the inflatable and deflatable cartridge, thereby attaching the cartridge receiving portion to the inflatable and deflatable cartridge; wherein the actuating mechanism is operable to displace the first and second arms between an open state corresponding to an inflated state of the inflatable and deflatable cartridge when positioned in the cartridge receiving portion and a closed state corresponding to a deflated state of the inflatable and deflatable cartridge when positioned in the cartridge receiving portion; wherein at the closed state, the first and the second receptacles extend parallel to each other; and wherein said first and the second receptacles are configured to slidingly engage a corresponding one of a first and a second catcher of the inflatable and deflatable cartridge in a direction along a device longitudinal axis of the device.

2. The device according to claim 1, wherein the cartridge receiving portion defines a volume configured to contain at least an inflatable and deflatable portion of the inflatable and deflatable cartridge, said volume being expandable and contractable by means of said actuating mechanism.

3. The device according to claim 1, wherein the first and the second receptacles are elongated receptacles extending along length of the corresponding arms, formed either as a single elongated receptacle or constituted by two or more discrete receptacles positioned along said length.

4. The device according to claim 1, wherein said first and second receptacles extend along at least a majority of the cartridge receiving portion in a direction along a device longitudinal axis of the device.

5. The device according to claim 1, wherein said first and second receptacles extend along whole of length of the cartridge receiving portion in a direction along a device longitudinal axis of the device.

6. The device according to claim 1, wherein each of said first and second receptacles has a length corresponding to respective catcher of the inflatable and deflatable cartridge.

7. The device according to claim 1, wherein said first and second receptacles are at least partially aligned with respect to each other in a plane extending along a device longitudinal axis of the device.

8. The device according to claim 1, wherein at the closed state, said volume is contracted and at the open state, said volume is expanded.

9. An inflatable and deflatable cartridge for use with a respiratory support device, said cartridge being configured to be removably received in the respiratory support device, and to be selectively inflated and deflated by an actuating mechanism of the respiratory support device, when received in the respiratory support device, to inhale air, when inflated, and exhale the air, when deflated, said cartridge comprising a first support base, a second support base spaced from the first support base in a direction perpendicular to a cartridge longitudinal axis of the cartridge, and an inflatable and deflatable bag portion disposed between, and fixedly connected to, the first and the second support bases, wherein the first support base comprises a first catcher configured to removably engage within a corresponding first receptacle of the respiratory support device, and the second support base comprises a second catcher configured to be removably received within a corresponding second receptacle of the respiratory wherein the actuating mechanism is operable to displace the first and second arms between an open state corresponding to an inflated state of the inflatable and deflatable cartridge when positioned in the cartridge receiving portion and a closed state corresponding to a deflated state of the inflatable and deflatable cartridge when positioned in the cartridge receiving portion; wherein at the closed state, the first and the second receptacles extend parallel to each other; and wherein said first and the second receptacles are configured to slidingly engage a corresponding one of a first and a second catcher of the inflatable and deflatable cartridge in a direction along a device longitudinal axis of the device.

10. The cartridge according to claim 9, wherein the first and the second catchers are elongated catchers extending along length of the corresponding bases in a direction along the cartridge longitudinal axis, formed either as a single elongated catcher or constituted by two or more discrete catchers positioned along said length.

11. The cartridge according to claim 10, wherein the first and second catchers extend along at least a majority of length of the respective support base.

12. The cartridge according to claim 10, wherein the first and second catchers extend along almost whole of length of the respective support base.

13. The cartridge according to claim 9, wherein length of each of the first and second catchers correspond to length of the corresponding receptacle of the respiratory support device.

14. A respiratory support device for operating an inflatable and deflatable bag to inhale and exhale air, said device comprising:

an actuating mechanism configured for selectively inflating and deflating said inflatable and deflatable bag;

a first arm having a first proximal portion constituting at least a part of the actuating mechanism, a first distal portion spaced from said first proximal portion along a device longitudinal axis of the device, and a first central portion between the first proximal and distal portions; and a second arm having a second proximal portion constituting at least a part of the actuating mechanism, a second distal portion spaced from said second proximal portion along the device longitudinal axis and defining together with the first distal portion a volume configured to be expandable and contractable by means of said actuating mechanism, and a second central portion between the second proximal and distal portions; wherein said first and second arms cross each other and are pivotally connected to each other at said respective central portions, said actuating mechanism being operable to pivot the first and second arms with respect to each other, wherein the device is configured to be used with a removable inflatable and deflatable cartridge, wherein the inflatable and deflatable bag constitutes an inflatable and deflatable portion of the inflatable and deflatable cartridge, and comprises a cartridge receiving portion defined by said volume between the first and second distal portions, said cartridge receiving portion being configured for removably attaching to the inflatable and deflatable cartridge, wherein the first distal portion comprises a first receptacle facing the second arm, and the second distal portion comprises a second receptacle facing the first arm, wherein said first and the second receptacles define at least partially the cartridge receiving portion, and wherein each of the first and the second receptacles is configured to removably engage a corresponding one of a first and a second catcher of the inflatable and deflatable cartridge, thereby attaching the cartridge receiving portion to the inflatable and deflatable cartridge, and wherein each of the first and the second receptacles is configured to removably engage a corresponding one of a first and a second catcher of the inflatable and deflatable cartridge, thereby attaching the cartridge receiving portion to the inflatable and deflatable cartridge, wherein the actuating mechanism is operable to pivot the first and second arms for displacing the device between an open state corresponding to an inflated state of the inflatable and deflatable bag and a closed state corresponding to a deflated state of the inflatable and deflatable bag; wherein at the closed state, the first and the second receptacles extend parallel to each other; and wherein said first and the second receptacles are configured to slidingly engage the corresponding one of the first and the second catcher of the inflatable and deflatable cartridge in a direction along a device longitudinal axis of the device.

* * * * *